(12) United States Patent
Iwahashi et al.

(10) Patent No.: US 8,285,028 B2
(45) Date of Patent: Oct. 9, 2012

(54) INSPECTION APPARATUS AND INSPECTION METHOD

(75) Inventors: Takashi Iwahashi, Osaka (JP); Toshihiko Tsujikawa, Osaka (JP); Atsushi Katayama, Kyoto (JP)

(73) Assignee: Panasonic Corporation, Osaka (JP)

( * ) Notice: Subject to any disclaimer, the term of this patent is extended or adjusted under 35 U.S.C. 154(b) by 301 days.

(21) Appl. No.: 12/679,363

(22) PCT Filed: Sep. 24, 2008

(86) PCT No.: PCT/JP2008/002623
§ 371 (c)(1),
(2), (4) Date: Mar. 22, 2010

(87) PCT Pub. No.: WO2009/041016
PCT Pub. Date: Apr. 2, 2009

(65) Prior Publication Data
US 2010/0220918 A1    Sep. 2, 2010

(30) Foreign Application Priority Data
Sep. 28, 2007   (JP) .................. 2007-256144

(51) Int. Cl.
*G01B 11/14* (2006.01)
*G06K 9/00* (2006.01)
*G06K 9/36* (2006.01)

(52) U.S. Cl. ......... 382/141; 382/151; 382/291; 356/614

(58) Field of Classification Search ........... 382/100–154
See application file for complete search history.

(56) References Cited

U.S. PATENT DOCUMENTS 4,397,554 A * 8/1983 Genco et al. .............. 356/239.1
4,687,338 A * 8/1987 Task et al. ..................... 356/446
4,794,648 A * 12/1988 Ayata et al. ................... 382/151
5,050,111 A * 9/1991 Ayata et al. ................... 700/302
(Continued)

FOREIGN PATENT DOCUMENTS
JP          7-273497          10/1995
(Continued)

OTHER PUBLICATIONS

International Search Report issued Dec. 26, 2008 in International (PCT) Application No. PCT/JP2008/002623.

*Primary Examiner* — Gregory J Toatley
*Assistant Examiner* — Jarreas C Underwood
(74) *Attorney, Agent, or Firm* — Wenderoth, Lind & Ponack, L.L.P.

(57) ABSTRACT

Aims to provide an inspection apparatus which precisely detects an amount of misalignment of a component mounted on a panel through an adhesive which contains conductive particles. The inspection apparatus includes: an infrared-light illuminator (305) which is provided on a bottom-surface side of the panel and illuminates with light a panel recognition mark formed on the panel and a component recognition mark formed on the component; an IR camera (307) which is provided opposite to the illuminator (305) and captures images of the light-illuminated recognition marks; and an amount-of-misalignment calculation unit (446) which calculates, using the images captured by the camera (307), an amount of misalignment of the recognition marks as an amount of misalignment in mounting position, wherein the illuminator (305) emits light in an amount which causes halation, the light having a wavelength that allows the light to pass through the panel and the component but does not allow or does not easily allow the light to pass through the conductive particles.

14 Claims, 10 Drawing Sheets

U.S. PATENT DOCUMENTS

| | | | |
|---|---|---|---|
| 5,854,745 | A | 12/1998 | Muraoka et al. |
| 5,858,806 | A | 1/1999 | Nishida |
| 6,349,153 | B1 * | 2/2002 | Teo ................................ 382/294 |

FOREIGN PATENT DOCUMENTS

| | | |
|---|---|---|
| JP | 8-128811 | 5/1996 |
| JP | 8-330393 | 12/1996 |
| JP | 2000-276233 | 10/2000 |
| JP | 3323395 | 9/2002 |
| JP | 2004-28930 | 1/2004 |
| JP | 2004-31868 | 1/2004 |
| JP | 2006-40978 | 2/2006 |

* cited by examiner

FIG. 6
(a)
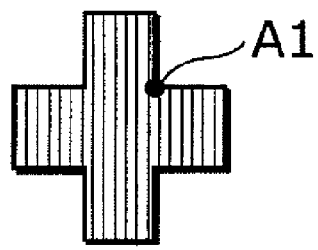
(b) 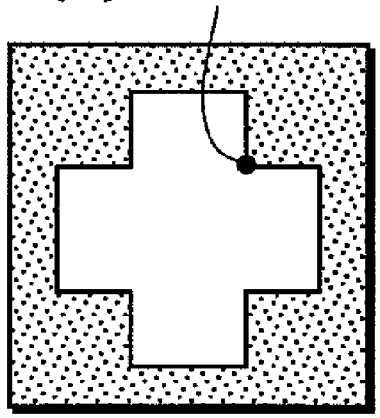   (c) 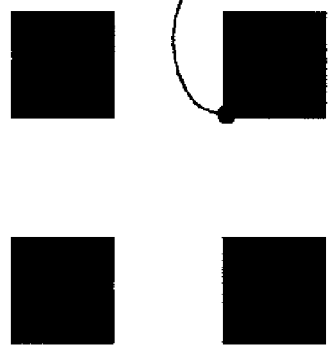
(d) 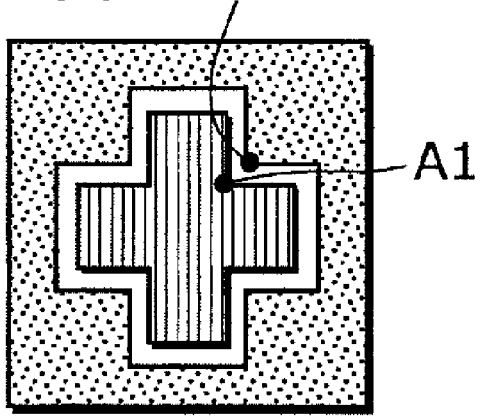   (e) 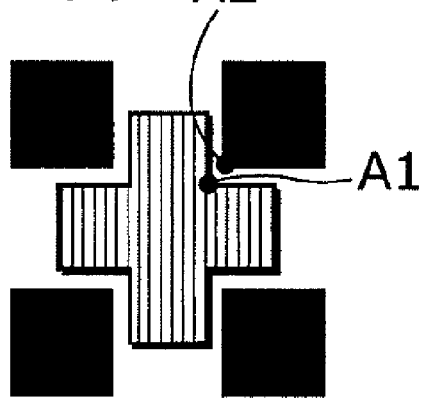

INSPECTION APPARATUS AND INSPECTION METHOD

TECHNICAL FIELD

The present invention relates to inspection apparatuses and inspection methods, and particularly to an inspection apparatus and an inspection method for inspecting a mounting status of an electronic component mounted on a substrate.

BACKGROUND ART

Conventionally, electronic components (hereinafter referred to as components), such as tape automated bonding (TAB) substrates, semiconductor elements, and flexible substrates which have an electrode, are mounted on flat panel displays (hereinafter referred to as panels) such as liquid crystal displays and plasma displays which have an electrode made of indium tin oxide (ITO) and the like.

This mounting involves temporary and permanent compression-bonding of a component to a panel while providing an anisotropic conductive film (hereinafter referred to as an ACF) between the component and the panel, so as to bond the electrode of the panel (hereinafter referred to as a panel electrode) and the electrode of the component (hereinafter referred to as a component electrode). The temporary compression-bonding involves softly pressing the component using a thermocompression-bonding head, and the permanent compression-bonding following the temporary compression-bonding involves pressing the temporary compression-bonded component using a thermocompression-bonding head under a pressure and a temperature higher than in the temporal compression-bonding. Then, an amount of relative misalignment (amount of misalignment) of the component from a predetermined mounting position is detected by an inspection apparatus. The detected amount of misalignment is provided as feedback for the next mounting of a component on the panel, and the mounting is performed in which the misalignment is corrected.

An example of the inspection apparatus which detects the amount of component misalignment is one disclosed in Patent Reference 1. The inspection apparatus disclosed in Patent Reference 1 detects an amount of component misalignment by detecting an amount of misalignment of the panel electrode and the component electrode (bump).
Patent Reference 1: Japanese Unexamined Patent Application Publication No. 08-330393

SUMMARY OF THE INVENTION

Problems that Invention is to Solve

With the inspection apparatus disclosed in Patent Reference 1, the positions of the panel electrode and the component electrode are calculated by an operator based on an image of the panel electrode and the component electrode captured by an imaging apparatus which is provided on the side of the panel's bottom surface (the surface of the panel on which the component is not mounted). Thus, with this inspection apparatus, it is very difficult to precisely detect an amount of misalignment of a component mounted on the panel through an adhesive, such as the ACF, which contains conductive particles. That is to say, light does not pass or does not easily pass through the conductive particles such as a metal, and thus light from the component electrode does not easily reach the imaging apparatus provided on the panel's bottom surface side, making it impossible to capture an image of the entire component electrode. As a consequence, the operator cannot easily recognize the position of the component electrode, resulting in inability to precisely calculate the amount of misalignment. When the mounting pitch of components becomes narrower, the conductive particles become smaller and denser, making it more likely for the light to be shielded by the conductive particles, which means that it is more difficult for the light to reach the imaging apparatus. As a result, it is difficult to recognize the component electrode through the conductive particles, and thus the problem becomes more significant when the mounting pitch becomes narrower.

In view of the above problem, an object of the present invention is to provide an inspection apparatus and an inspection method for precisely detecting an amount of misalignment of a component mounted on a panel through an adhesive which contains conductive particles.

Means to Solve the Problems

To achieve the above object, the inspection apparatus according to an aspect of the present invention is an inspection apparatus which detects an amount of misalignment, from a predetermined mounting position, of a component mounted on a surface of a panel through an adhesive which contains conductive particles, the inspection apparatus including: an illuminator which is provided on a bottom surface side of the panel which is opposite to a side of the panel on which the component is mounted, and illuminates with light a panel recognition mark formed on the panel and a component recognition mark formed on the component; a camera which is provided on a side of the panel opposite to the illuminator and captures an image of the panel recognition mark and an image of the component recognition mark which are illuminated with the light; and a calculation unit configured to calculate, using the images captured by the camera, an amount of misalignment in a positional relationship between the panel recognition mark and the component recognition mark from a predetermined positional relationship, wherein the illuminator emits light in an amount which causes halation in the images, the light having a wavelength that allows the light to pass through the panel and the component but does not allow or does not easily allow the light to pass through the conductive particles.

Here, the illuminator emits light in an amount which causes an average particle diameter of the conductive particles in the images to be 80% or below of an actual average particle diameter. Further, the illuminator may emit light in an amount which causes a minimum luminance value to be higher than 15% of a maximum luminance value in a portion of the images other than portions of the panel recognition mark and the component recognition mark.

With this, the panel recognition mark and the component recognition mark are illuminated with light intense enough to cause halation, so as to capture the image of the panel recognition mark and the image of the component recognition mark. Thus, it is possible to prevent a situation where the panel recognition mark and the component recognition mark cannot be recognized due to the conductive particles, thereby allowing calculation of an amount of misalignment of the component through reduction in the impact of the conductive particles. This enables reliable detection of the amount of misalignment of the component mounted on the panel through the adhesive containing the conductive particles.

Further, the inspection apparatus calculates the amount of component misalignment based on the captured images of the panel recognition mark and the component recognition mark.

Therefore, it is possible to precisely detect the amount of misalignment of the component mounted on the panel through the adhesive containing the conductive particles.

The inspection apparatus may further include a focus adjustment unit configured to adjust a focus of the camera to one of the panel recognition mark and the component recognition mark and then to shift the focus of the camera by a predetermined amount.

With this, even when adjusting the focus to one of the recognition marks makes the outline of the other one of the recognition marks unclear in the image, shifting the focus of the camera allows the outline of the other one of the recognition marks to appear clearly.

The inspection apparatus further includes a determination unit configured to determine whether or not a feature point of the panel recognition mark and a feature point of the component recognition mark are recognizable in the images, wherein the focus adjustment unit is configured to shift the focus of the camera when the determination unit determines that the feature points are not recognizable.

In addition, the inspection apparatus may further include an obtaining unit configured to obtain a position of the feature point of the panel recognition mark and a position of the feature point of the component recognition mark in the images, wherein the calculation unit is configured to calculate an amount of misalignment of the feature point of one of the panel recognition mark and the component recognition mark from a predetermined position that is determined using the position of the feature point of the other one of the recognition marks as a reference.

As a result, even when the feature points are not recognizable due to the conductive particles, shifting the focus makes the feature points obtainable. Thus, calculation of the amount of component misalignment is possible through reduction in the impact of the conductive particles, thereby enabling reliable detection of the amount of misalignment of the component mounted on the panel through the conductive particles.

Further, the camera may be an infrared camera, and the illuminator may be an infrared light illuminator.

With this, a special illuminator or a special camera are not necessary, thereby preventing increase in the size and complication of the apparatus.

The present invention can also be realized as an inspection method for detecting an amount of misalignment, from a predetermined mounting position, of a component mounted on a surface of a panel through an adhesive which contains conductive particles, the inspection method including: illuminating with light a panel recognition mark formed on the panel and a component recognition mark formed on the component, using an illuminator provided on a bottom surface side of the panel which is opposite to a side of the panel on which the component is mounted; capturing an image of the panel recognition mark and an image of the component recognition mark which are illuminated with the light, using a camera provided on a side of the panel opposite to the illuminator; and calculating, using the images captured in by the camera in the capturing, an amount of misalignment in a positional relationship between the panel recognition mark and the component recognition mark from a predetermined positional relationship, wherein in the illuminating, light is emitted in an amount which causes halation in the images, the light having a wavelength that allows the light to pass through the panel and the component but does not allow or does not easily allow the light to pass through the conductive particles.

Here, in the illuminating, light may be emitted in an amount which causes an average particle diameter of the conductive particles in the images to be 80% or below of an actual average particle diameter. Further, in the illuminating, light may be emitted in an amount which causes a minimum luminance value to be higher than 15% of a maximum luminance value in a portion of the images other than portions of the panel recognition mark and the component recognition mark. As a result, it is possible to precisely and reliably detect the amount of misalignment of the component mounted on the panel through the adhesive containing the conductive particles.

Effects of the Invention

The present invention provides an inspection apparatus and an inspection method for precisely and reliably detecting an amount of misalignment of a component mounted on a panel through an adhesive which contains conductive particles.

BRIEF DESCRIPTION OF DRAWINGS

FIG. 6 The part (a) of FIG. 6 shows an example of a component recognition mark. The part (b) of FIG. 6 shows an example of a panel recognition mark. The part (c) of FIG. 6 shows an example of a panel recognition mark. The part (d) of FIG. 6 shows an example of a component recognition mark and a panel recognition mark. The part (e) of FIG. 6 shows an example of a component recognition mark and a panel recognition mark.

NUMERICAL REFERENCES

Figure 1:
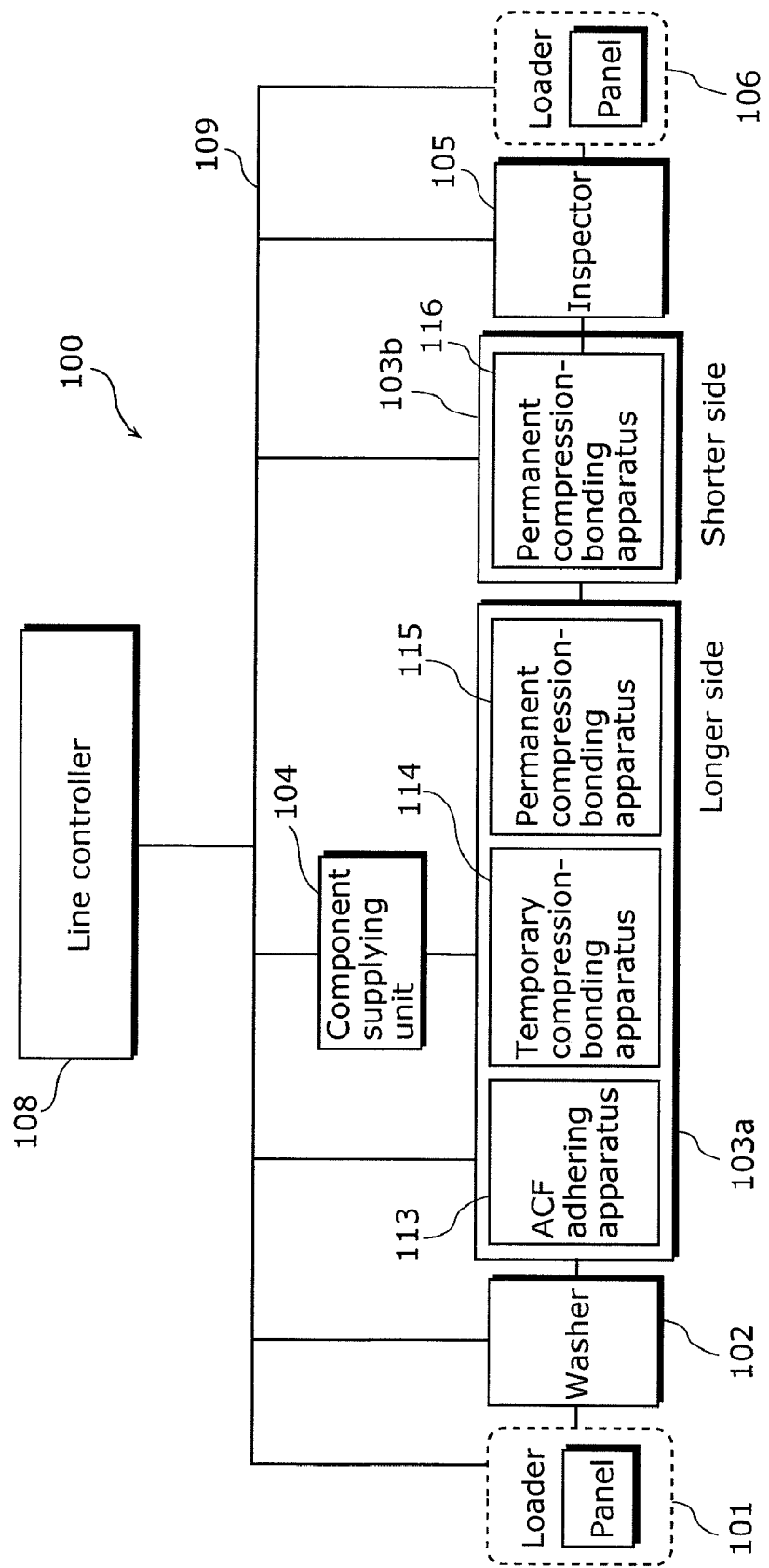
FIG. 1 is a conceptual diagram showing an entire configuration of a component mounting system according to an embodiment of the present invention.

100 Component mounting system
101, 106 Loader
102 Washer
103a, 103b Panel mounter
104 Component supplying unit
105 Inspector
108 Line controller
109 Communication cable
113 ACF adhering apparatus
114 Temporary compression-bonding apparatus 115, 116 Permanent compression-bonding apparatus
200 Panel
201 Component
202, 204, 206 Thermocompression-bonding head
203, 205, 207, 301 Back-up stage
210 ACF
211 Conductive particles
300 Mounting-completed panel
302 Panel transfer stage unit
303 Under-panel transfer shaft unit
305 Infrared light illuminator
307 IR camera
410, 430, 440 Control unit
411, 431, 441 Storage unit
411a Master table
412, 432, 442 Input unit
413, 433, 443 Display unit
414, 434, 444 Communication I/F unit
415 Operation unit
431a Feedback data
435, 445 Mechanical unit
436 Data updating unit
441a Inspection position data
441b Feature point data
446 Amount-of-misalignment calculation unit
447 Correction unit
448 Obtaining unit
449 Determination unit
450 Focus adjustment unit

DETAILED DESCRIPTION OF THE INVENTION

Hereinafter, a component mounting system according to an embodiment of the present invention is described with reference to the drawings.

FIG. 1 is a conceptual diagram showing an entire configuration of a component mounting system 100 of the present embodiment.

The component mounting system 100 includes a line including: a loader 101; a washer 102; two panel mounters 103a and 103b; a component supplying unit 104; an inspector 105; and a loader 106, a line controller 108, and a communication cable 109.

The loader 101 supplies a panel to the line. The washer 102 washes a part of the panel supplied by the loader 101, where the ACF is to be adhered. The two panel mounters 103a and 103b mount components on different sides of the panel. The component supplying unit 104 supplies a component to the panel mounter 103a. The inspector 105 detects an amount of relative misalignment (amount of misalignment) of a component mounted on the top surface of the panel through the ACF, from a predetermined mounting position of the component. The loader 106 ejects the panel on which the components have been mounted (hereinafter referred to as a mounting-completed panel). The line controller 108 manages and controls communication and so on of various data and the operating status of the line as a whole. The communication cable 109 connects the line controller 108 with each element of the line.

The panel mounter 103a includes an ACF adhering apparatus 113, a temporary compression-bonding apparatus 114, and a permanent compression-bonding apparatus 115. The ACF adhering apparatus 113 applies an ACF to a longer side and a shorter side of the panel's top surface. The temporary compression-bonding apparatus 114 places a component using a thermocompression-bonding head, and softly presses the component to temporarily compression-bond the component to the panel's top surface. The permanent compression-bonding apparatus 115 presses the component, which has been temporarily compression-bonded to the longer side of the panel's top surface, using a thermocompression-bonding head under a pressure and a temperature higher than in the temporal compression-bonding, so as to permanently compression-bond the component to the panel's top surface.

The panel mounter 103b includes a permanent compression-bonding apparatus 116. The permanent compression-bonding apparatus 116 presses the component, which has been temporarily compression-bonded to the shorter side of the panel's top surface, using a thermocompression-bonding head under a pressure and a temperature higher than in the temporal compression-bonding, so as to permanently compression-bond the component to the panel's top surface.

Figure 2:
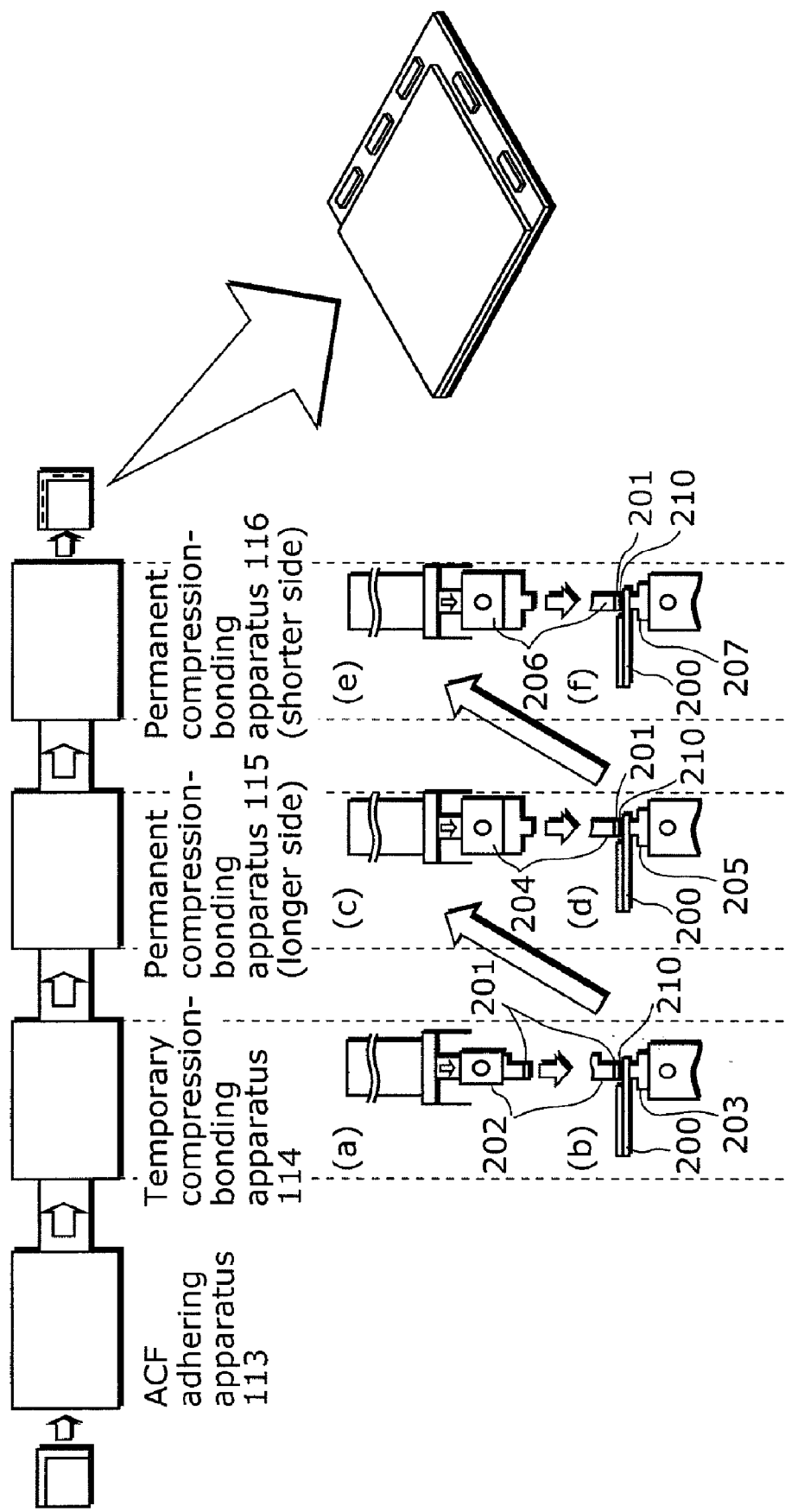
FIG. 2 shows how panel mounters of the component mounting system mount components on a panel.

FIG. 2 shows how the panel mounters 103a and 103b mount components on the panel.

First, the ACF adhering apparatus 113 applies an ACF 210 at the edges of the top surface of a panel 200, and then transfers the panel 200 to the temporary compression-bonding apparatus 114.

Next, the temporary compression-bonding apparatus 114 lowers a thermocompression-bonding head 202 holding a component 201 ((a) in FIG. 2), and temporarily compression-bonds the component 201 to the region of the top surface of the panel 200 placed on a back-up stage 203, to which the ACF 210 has been adhered ((b) in FIG. 2).

Next, after the panel 200 is transferred to the permanent compression-bonding apparatus 115, the permanent compression-bonding apparatus 115 lowers a thermocompression-bonding head 204 ((c) in FIG. 2) and permanently compression-bonds the component 201 which has been temporarily compression-bonded to the longer side of the top surface of the panel 200 placed on a back-up stage 205 ((d) in FIG. 2).

Lastly, after the panel 200 is transferred to the permanent compression-bonding apparatus 116, the permanent compression-bonding apparatus 116 lowers a thermocompression-bonding head 206 ((e) in FIG. 2) and permanently compression-bonds the component 201 which has been temporarily compression-bonded to the shorter side of the top surface of the panel 200 placed on a back-up stage 207 ((f) in FIG. 2).

Figure 3:
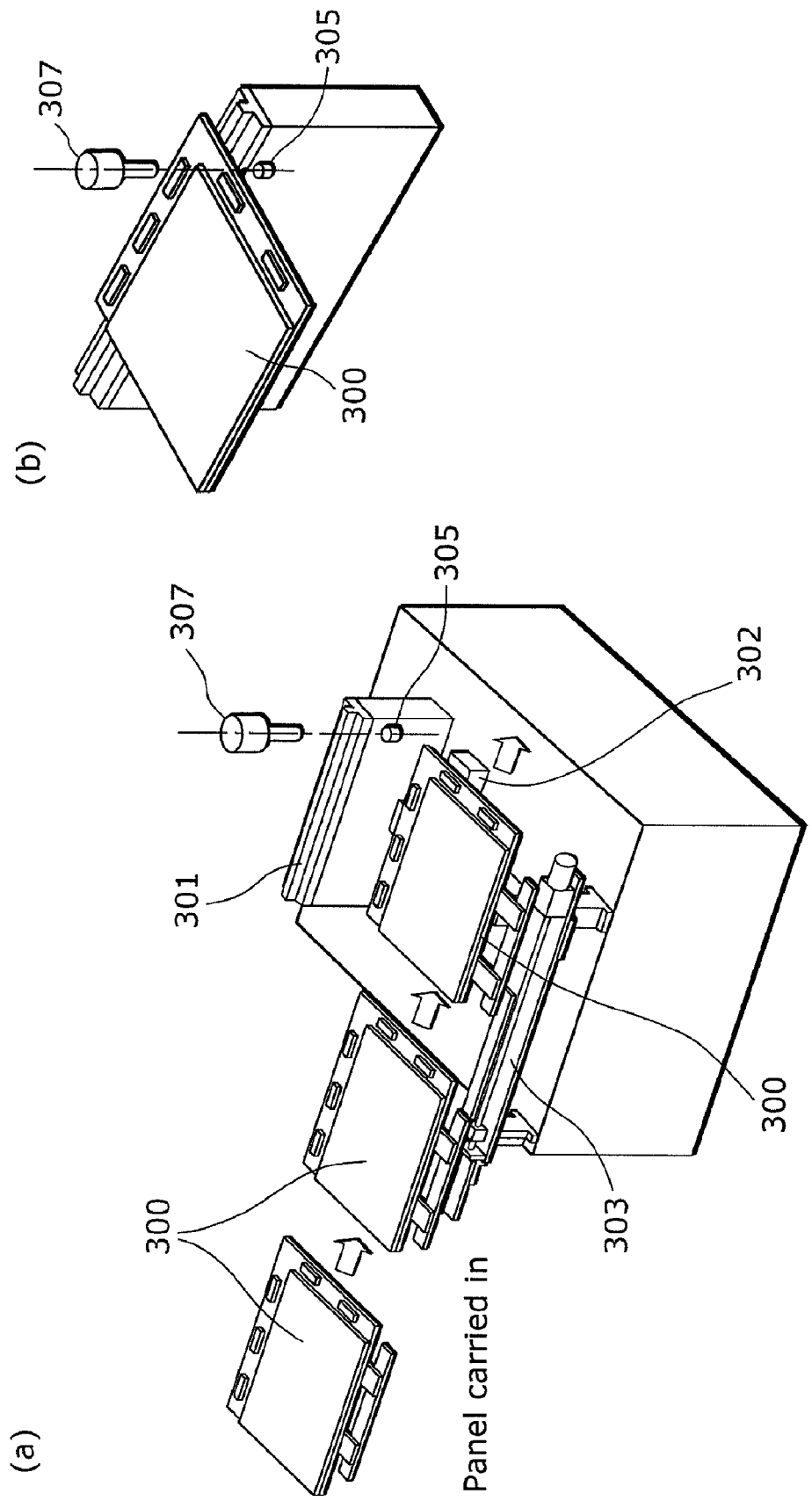
FIG. 3 The part (a) of FIG. 3 is a perspective view showing a schematic configuration of an inspector of the component mounting system. The part (b) of FIG. 3 shows how an inspector of the component mounting system inspects a mounting-completed panel.

The part (a) of FIG. 3 is a perspective view showing a schematic configuration of the inspector 105, and the part (b) of FIG. 3 shows how the inspector 105 inspects a mounting-completed panel 300.

The inspector 105 includes a back-up stage 301, a panel transfer stage unit 302, an under-panel transfer shaft unit 303, an infrared light illuminator 305, and an infrared (IR) camera 307.

The mounting-completed panel 300 is placed on the back-up stage 301. The panel transfer stage unit 302 transfers the mounting-completed panel 300 to the back-up stage 301. The under-panel transfer shaft unit 303 transfers the mounting-completed panel 300 to the panel transfer stage unit 302.

The infrared light illuminator 305 is provided on the side of the bottom surface of the mounting-completed panel 300 (the surface of the mounting-completed panel 300 on which the components are not mounted), and illuminates the bottom surface of the mounting-completed panel 300 with infrared light. The mounting-completed panel 300 is transparent to infrared light, and thus the infrared light emitted by the infrared light illuminator 305 passes through the mounting-completed panel 300 to illuminate a panel recognition mark formed on the top surface of the mounting-completed panel 300 (the surface of the mounting-completed panel 300 on which the components are mounted). The infrared light does not pass or does not easily pass through conductive particles which are contained in the ACF and are 2 to 9 μm in diameter, for example. Thus, the infrared light emitted by the infrared light illuminator 305 only illuminates a part of a component recognition mark formed on the component's top surface (the surface of the component bonded to the panel). The component is transparent to infrared light, and thus the infrared light emitted by the infrared light illuminator 305 partially passes through the component.

The IR camera 307 is provided on the side of the component's bottom surface (the surface of the component opposite to the surface bonded to the panel). The IR camera 307 captures an image of the panel recognition mark and an image of the component recognition mark which are illuminated with the infrared light.

Here, the panel is primarily made of glass, the panel recognition mark and the component recognition mark are primarily made of Al, and the surface of the conductive particles is primarily made of Ni.

The infrared light illuminator 305 and the IR camera 307 are arranged on the same axis, and face each other with the mounting-completed panel 300 therebetween. Here, being arranged on the same axis means that the optical axis of the infrared light illuminator 305 (illuminating direction) and the optical axis of the IR camera 307 (image capturing direction) are substantially on the same straight line.

Figure 4:
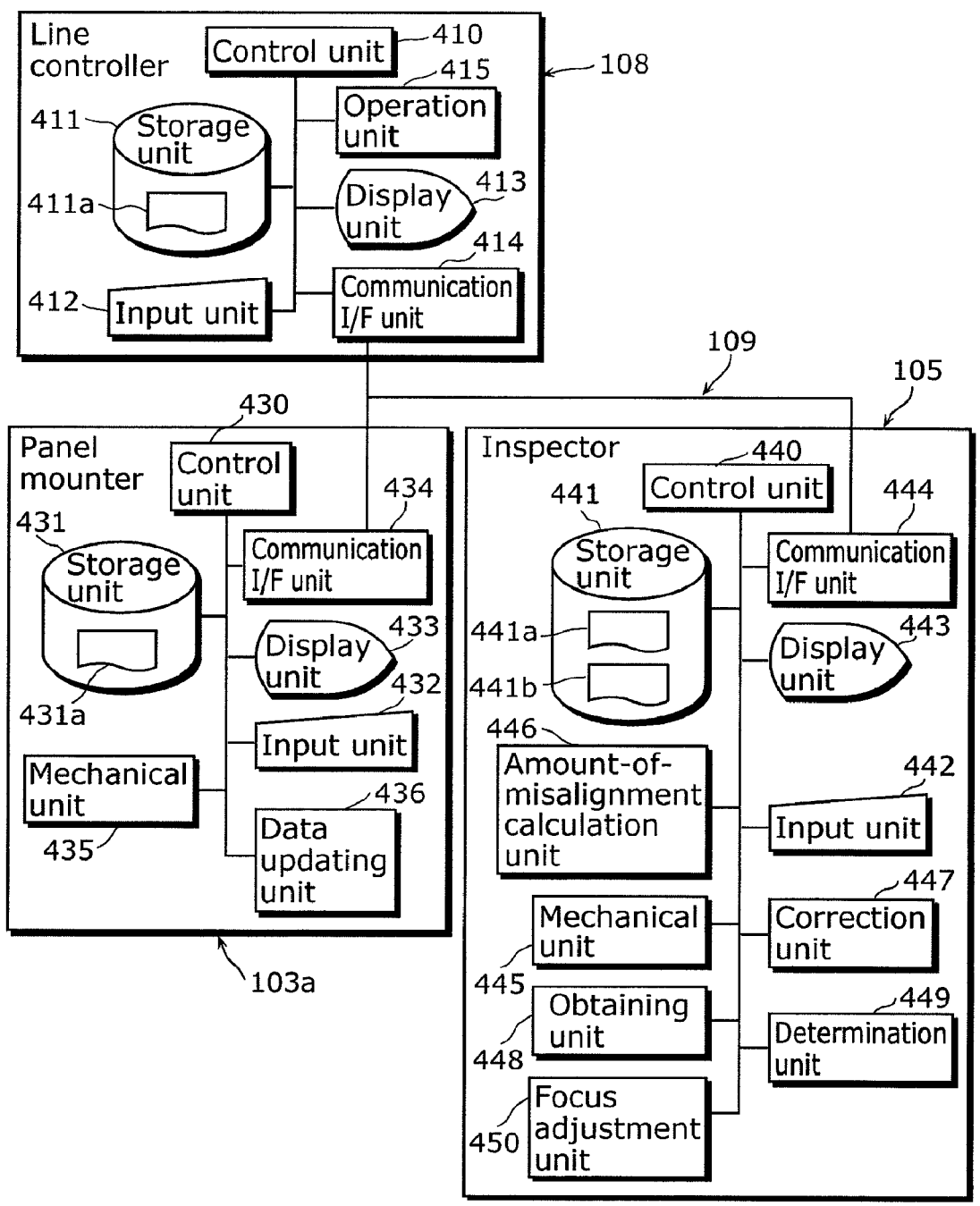
FIG. 4 is a functional block diagram showing a schematic configuration of the component mounting system.

FIG. 4 is a functional block diagram showing a schematic configuration of the component mounting system 100.

The line controller 108 includes a control unit 410, a storage unit 411, an input unit 412, a display unit 413, a communication I/F unit 414, and an operation unit 415.

According to an instruction or the like from an operator, the control unit 410 executes line control data stored in the storage unit 411, and controls each unit based on the execution result.

The storage unit 411 is a hard disk and a memory, for example, and holds line control data, a master table 411a, and so on. The master table 411a contains information indicating an associated pair of a mounting position and an amount of correction (feedback amount).

The input unit 412 is a keyboard and a mouse, for example, and the display unit 413 is a cathode-ray tube (CRT), a liquid crystal display (LCD), and the like. These units are used for communication and so on between the line controller 108 and the operator.

The communication I/F unit 414 is a local area network (LAN) adapter, for example, and is used for communication and so on between: the line controller 108; and the panel mounter 103a and the inspector 105.

The operation unit 415 calculates an amount of correction based on the amount of component misalignment calculated by the inspector 105, and updates the master table 411a stored in the storage unit 411.

The panel mounter 103a includes a control unit 430, a storage unit 431, an input unit 432, a display unit 433, a communication I/F unit 434, a mechanical unit 435, and a data updating unit 436.

According to an instruction or the like from the operator, the control unit 430 executes NC data stored in the storage unit 431, and controls each unit based on the execution result.

The storage unit 431 is a hard disk and a memory, for example, and holds NC data, feedback data 431a, and so on. The feedback data 431a contains information indicating an associated pair of a mounting position and an amount of correction.

The input unit 432 is a keyboard and a mouse, for example, and the display unit 433 is a CRT, an LCD, and the like. These units are used for communication and so on between the panel mounter 103a and the operator.

The communication I/F unit 434 is a LAN adapter, for example, and is used for communication and so on between the panel mounter 103a and the line controller 108.

The mechanical unit 435 is a set of mechanical components including a thermocompression-bonding head, a transport unit, an arm, an XY table, a component supplying unit, a motor which drives these components, and a motor controller, for example.

The data updating unit 436 updates the feedback data 431a stored in the storage unit 431 based on the master table 411a transmitted by the line controller 108.

The inspector 105 includes a control unit 440, a storage unit 441, an input unit 442, a display unit 443, a communication I/F unit 444, a mechanical unit 445, an amount-of-misalignment calculation unit 446, a correction unit 447, an obtaining unit 448, a determination unit 449, and a focus adjustment unit 450.

According to an instruction or the like from the operator, the control unit 440 executes NC data stored in the storage unit 441, and controls each unit based on the execution result.

The storage unit 441 is a hard disk and a memory, for example, and holds NC data, inspection position data 441a, feature point data 441b, and so on. The inspection position data 441a is a set of information indicating all positions to be inspected by the inspector 105. The feature point data 441b is information about a feature point of the component recognition mark.

The input unit 442 is a keyboard and a mouse, for example, and the display unit 443 is a CRT, an LCD, and the like. These units are used for communication and so on between the inspector 105 and the operator.

The communication I/F unit 444 is a LAN adapter, for example, and is used for communication and so on between the inspector 105 and the line controller 108.

The mechanical unit 445 is a set of mechanical components including a panel transfer stage unit, an under-panel transfer shaft unit, an infrared light illuminator, an IR camera, a motor which drives these components, and a motor controller, for example.

The amount-of-misalignment calculation unit 446 is an example of the calculation unit of the present invention, and calculates an amount of misalignment of the panel recognition mark and the component recognition mark in the images captured by the IR camera, from a predetermined mounting positional relationship when the component is mounted on the panel. To be more specific, the amount-of-misalignment calculation unit 446 calculates an amount of misalignment of a predetermined feature point of the component recognition mark, from a predetermined position that is determined using, as a reference, the position of a feature point of the panel recognition mark in the images captured by the IR camera.

The correction unit 447 corrects the images captured by the IR camera, through either linear interpolation or curve interpolation, and further corrects the images through binarization. More specifically, the correction unit 447 deletes conductive particles from the images captured by the IR camera, performs linear interpolation or curve interpolation to interpolate a part of the images, the outline of which has become unclear due to the deletion of the conductive particles, and further performs binarization.

The obtaining unit 448 is an example of the obtaining unit of the present invention, and obtains, from the images captured by the IR camera, a position of a predetermined feature point of the panel recognition mark and a position of a predetermined feature point of the component recognition mark.

The determination unit 449 is an example of the determination unit of the present invention, and determines whether or not predetermined feature points of the panel recognition mark and the component recognition mark are recognizable in the images captured by the IR camera.

The focus adjustment unit 450 is an example of the focus adjustment unit of the present invention, and adjusts the focus of the IR camera to make the predetermined feature point of the component recognition mark recognizable in the image captured by the IR camera. The focus of the IR camera is adjusted by vertically moving the IR camera. In the case where the IR camera has a focus adjustment function, the focus adjustment of the IR camera may be performed using the focus adjustment function.

Figure 5:
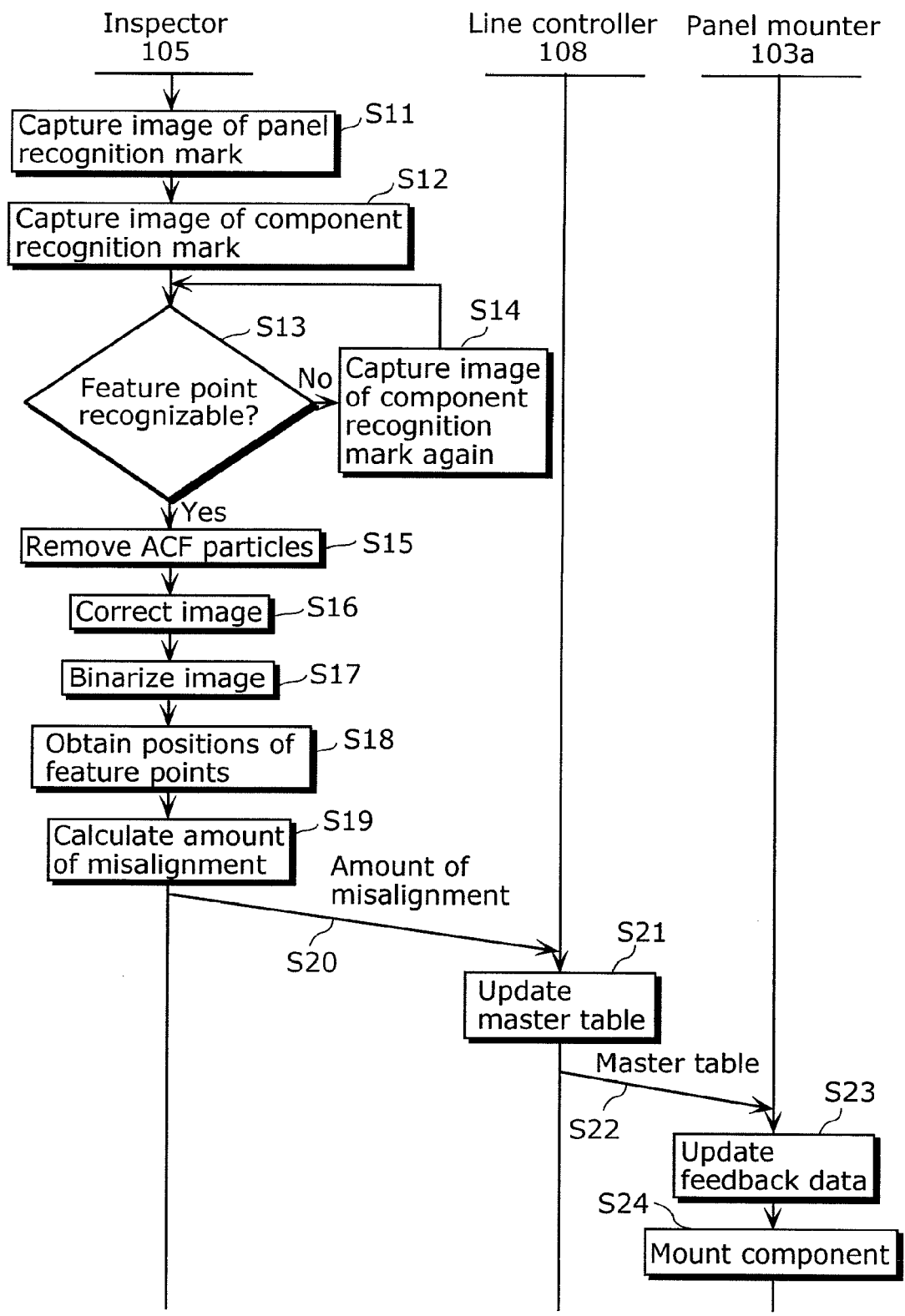
FIG. 5 shows a sequence of a feedback operation performed by the component mounting system.

Next, a feedback operation (providing feedback of an amount of component misalignment for the component mounting) performed by the component mounting system 100 is described in detail. FIG. 5 shows a sequence of the feedback operation performed by the component mounting system 100.

First, the control unit 440 of the inspector 105 causes the focus adjustment unit 450 to adjust the focus of the IR camera 307 to the panel recognition mark of the mounting-completed panel 300, and then causes the mechanical unit 445 to capture an image of the panel recognition mark of the mounting-completed panel 300 (Step S11). To be more specific, the control unit 440 of the inspector 105 causes the infrared light illuminator 305 to illuminate with infrared light the panel recognition mark formed at a position indicated in the inspection position data 441a, from the bottom surface side of the mounting-completed panel 300 which is opposite to the side of the mounting-completed panel 300 on which the components are mounted; and causes the IR camera 307 to capture an image of the panel recognition mark from the bottom surface side of the component opposite to the surface of the component adhered to the panel.

Here, the infrared light illuminator 305 illuminates the panel recognition mark with light intense enough to cause halation in images to be captured by the IR camera 307 (light intense enough for the IR camera 307 to capture images with halation), that is, light in an amount which causes the average particle diameter (average diameter) of the conductive particles in the images captured by the IR camera 307 to be 80% or below of the actual average particle diameter. For example, 30 to 60% of the conductive particles located between the panel electrode and the component electrode of the mounting-completed panel become flatly deformed due to the permanent compression-bonding, resulting in increase in the average particle diameter. However, the average particle diameter of the conductive particles in the captured images (the average particle diameter of black circles representing the conductive particles in the images) become as small as 80% or below of the average particle diameter prior to the flat deformation. In the case where the shape of the conductive particles in the captured images (the shape of the black circles representing the conductive particles in the images) is not a perfect circle, e.g. ellipse, the average diameter of perfect circles circumscribing the conductive particles in the images (the black circles representing the conductive particles in the images) is used as the average particle diameter of the conductive particles in the images.

Preferably, the mount of light is such that the average particle diameter (average diameter) of the conductive particles in the captured images becomes 30% or above of the actual average particle diameter. This is to allow recognition of the recognition marks without placing an excess burden on the infrared light illuminator 305.

Next, the control unit 440 of the inspector 105 causes the focus adjustment unit 450 to shift the focus of the IR camera 307 off the panel recognition mark by a predetermined amount, and then causes the mechanical unit 445 to capture an image of the component recognition mark of the component (Step S12). To be more specific, the control unit 440 of the inspector 105 causes the infrared light illuminator 305 to illuminate with infrared light the component recognition mark formed at a position indicated in the inspection position data 441a, from the bottom surface side of the mounting-completed panel 300 which is opposite to the side of the mounting-completed panel 300 on which the components are mounted; and causes the IR camera 307 to capture an image of the component recognition mark from the bottom surface side of the component which is opposite to the side of the component adhered to the panel. Here, too, the infrared light illuminator 305 illuminates the component recognition mark with light intense enough to cause halation.

Next, the control unit 440 of the inspector 105 causes the determination unit 449 to determine whether or not the captured image of the component recognition mark is a favorable image, that is, whether or not the image clearly shows the outline of the component recognition mark and the feature point of the component recognition mark is recognizable (Step S13).

For example, assume that a component recognition mark as shown in the part (a) of FIG. 6 is formed on the component, a panel recognition mark as shown in the part (b) or (c) of FIG. 6 is formed on the panel, and when the component is mounted at a predetermined mounting position on the panel, the component recognition mark and the panel recognition mark have such a positional relationship as shown in the part (d) or (e) of FIG. 6. In this case, assuming that the feature point data 441b indicates, as feature points, an edge (corner) A1 at which straight lines constituting the outline of the component recognition mark intersect and an edge (corner) A2 at which straight lines constituting the outline of the panel recognition mark intersect, it is determined whether or not the edge A1 is recognizable.

Figure 7:
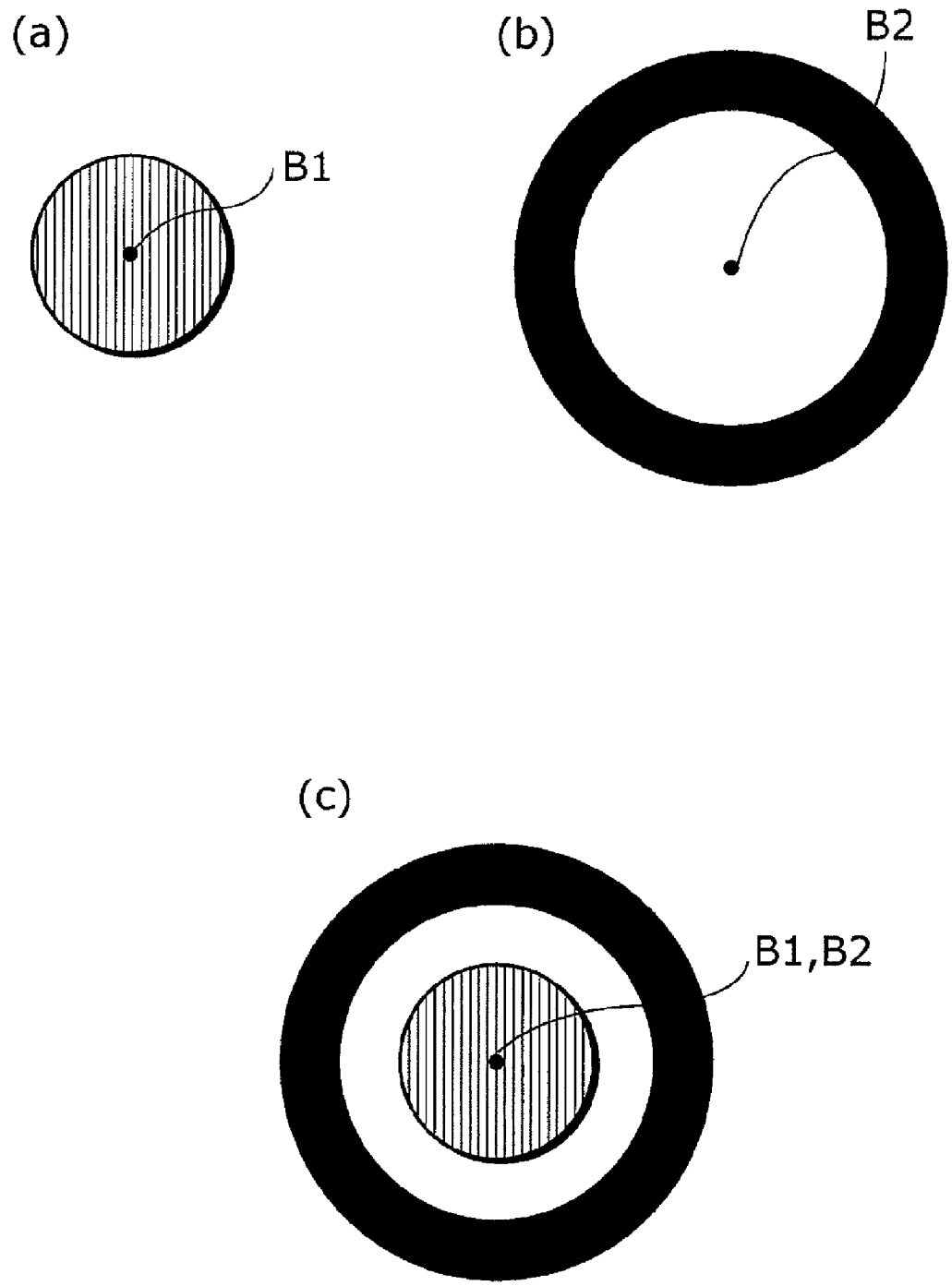
FIG. 7 The part (a) of FIG. 7 shows an example of a component recognition mark. The part (b) of FIG. 7 shows an example of a panel recognition mark. The part (c) of FIG. 7 shows an example of a component recognition mark and a panel recognition mark.

In addition, assume that a component recognition mark as shown in the part (a) of FIG. 7 is formed on the component, a panel recognition mark as shown in the part (b) of FIG. 7 is formed on the panel, and when the component is mounted at a predetermined mounting position on the panel, the component recognition mark and the panel recognition mark have such a positional relationship as shown in the part (c) of FIG. 7. In this case, assuming that the feature point data 441b indicates, as feature points, the center of gravity B1 of a circle constituting the component recognition mark and the center of gravity B2 of a circle constituting the panel recognition mark, it is determined whether or not the center of gravity B1 is recognizable.

Next, if it is determined that the captured image of the component recognition mark is not a favorable image (No in Step S13), the control unit 440 of the inspector 105 causes the focus adjustment unit 450 to further shift the focus of the IR camera 307 by a predetermined amount, and then causes the mechanical unit 445 to capture an image of the component recognition mark again (Step S14). In the case where the total amount by which the focus is shifted exceeds a predetermined threshold, it is handled as an image capturing error and the capturing of the image of the component recognition mark stops.

Figure 8:
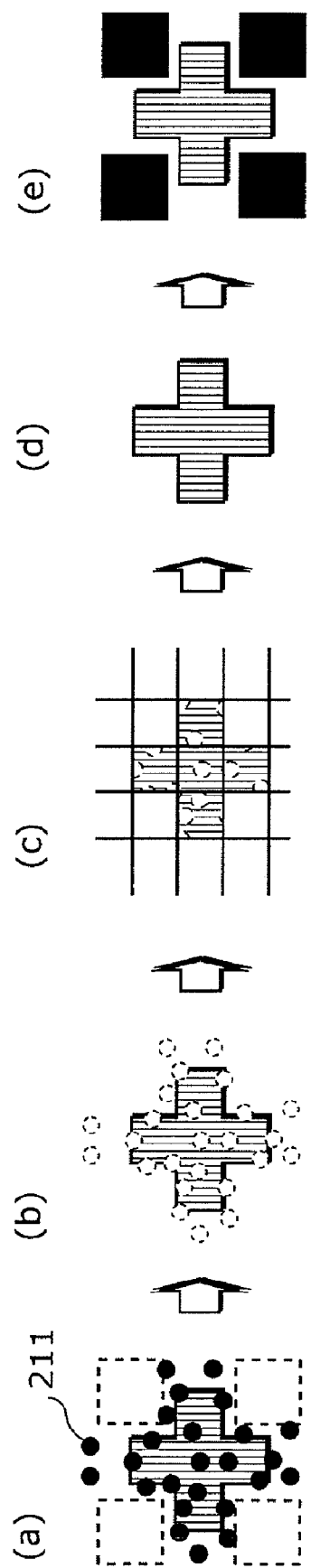
FIG. 8 shows how an inspector of the component mounting system corrects an image.

Next, if it is determined that the captured image of the component recognition mark is a favorable image (Yes in Step S13), the control unit 440 of the inspector 105 causes the correction unit 447 to delete the conductive particles 211 of the ACF 210 from the image as shown in the parts (a) and (b) of FIG. 8 (Step S15).

The deletion of the images of the conductive particles 211 from the image involves: storing in advance a plurality of images of the conductive particles 211 in the storage unit 441; comparing the conductive particles 211 in the captured image with the stored images; extracting from the captured image the conductive particles having a high degree of match with the stored images; and deleting the extracted conductive particles as the conductive particles 211. Alternatively, the conductive particles high in circularity, that is, the conductive particles whose length between the center of gravity and the outer edge is within a certain range, are extracted from the captured image, and the extracted conductive particles are deleted as images of the conductive particles 211.

Next, as shown in the part (c) of FIG. 8, the control unit 440 of the inspector 105 causes the correction unit 447 to correct the image from which the conductive particles 211 have been deleted, through either linear interpolation or curve interpolation of the parts from which the conductive particles 211 have been deleted (Step S16).

Next, as shown in the part (d) of FIG. 8, the control unit 440 of the inspector 105 causes the correction unit 447 to further correct the above corrected image through binarization to ensure a clear contrast (Step 517). This gives images, as shown in the part (e) of FIG. 8, from which the positions of the predetermined feature points of the panel recognition mark and the component recognition mark can be obtained.

Next, the control unit 440 of the inspector 105 causes the obtaining unit 448 to obtain the positions of the respective feature points (Step S18). To be more specific, the control unit 440 of the inspector 105 causes the obtaining unit 448 to obtain the position of the predetermined feature point of the panel recognition mark and the position of the feature point of the component recognition mark from the images on which the binarization has been performed.

Next, the control unit 440 of the inspector 105 causes the amount-of-misalignment calculation unit 446 to calculate, as an amount of misalignment of the mounted component, an amount of misalignment of the predetermined feature point of the component recognition mark from a predetermined position that is determined using the position of the feature point of the panel recognition mark as a reference (Step S19). More specifically, the control unit 440 of the inspector 105 causes the amount-of-misalignment calculation unit 446 to calculate the position of the predetermined feature point of the component recognition mark, which is determined using the position of the predetermined feature point of the panel recognition mark as a reference, and to calculate an amount of misalignment of the predetermined feature point of the component recognition mark located at the calculated position, from a predetermined position which is determined using the position of the predetermined feature point of the panel recognition mark as a reference.

Next, the control unit 440 of the inspector 105 causes the communication I/F unit 444 to transmit to the line controller 108 the calculated amount of component misalignment in association with a mounting position indicated in the inspection position data 441a (Step S20).

Next, the control unit 410 of the line controller 108 causes the operation unit 415 to update the master table 411a stored in the storage unit 411 based on the amount of misalignment received via the communication I/F unit 414 (Step S21).

Next, the control unit 410 of the line controller 108 causes the communication I/F unit 414 to transmit the updated master table 411a to the panel mounter 103a (Step S22).

Next, the control unit 430 of the panel mounter 103a updates the feedback data 431a stored in the storage unit 431 based on the master table 411a received via the communication I/F unit 434 (Step S23).

Lastly, the control unit 430 of the panel mounter 103a executes NC data and causes the mechanical unit 435 to mount the component on the panel (Step S24). The mounting involves correcting the mounting position of the component with the updated feedback data 431a taken into account, and mounting the component at the corrected mounting position.

As described above, the inspector 105 according to the present embodiment calculates an amount of component misalignment based on the image of the panel recognition mark and the image of the component recognition mark. This makes it possible to precisely detect the amount of misalignment of the component mounted on the panel through the ACF.

Further, the inspector 105 according to the present embodiment illuminates the panel recognition mark and the component recognition mark with light intense enough to cause halation, so as to capture an image of the panel recognition mark and an image of the component recognition mark. Due to the halation, the light surrounds the spherical conductive particles, causing the conductive particles to appear smaller and thus reducing the impact on the image recognition. This makes it possible to capture the image of the recognition mark of the flat panel and the image of the recognition mark of the component as the light is reflected. Therefore, the conductive particles allow the feature points of the panel recognition mark and the component recognition mark to be recognizable. As a result, the calculation of the amount of component misalignment is free from the impact of the conductive particles, making it possible to reliably detect the amount of misalignment of the component mounted on the panel through the ACF.

Figure 9:
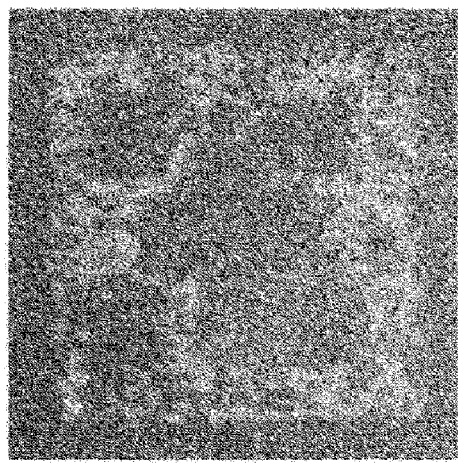
FIG. 9 shows an example of an image captured by an IR camera.

For example, when capturing an image of the panel recognition mark and an image of the component recognition mark using an ordinary amount of light, only such images as shown in FIG. 9 can be obtained in which the outlines of the recognition marks are unclear and the feature points are not recognizable and from which an amount of misalignment cannot be detected. However, when capturing an image of the panel recognition mark and an image of the component recognition mark using light intense enough to cause halation (amount of light which causes the average particle diameter of the conductive particles in the captured images to be 80% or below of the actual average particle diameter), such images as shown in FIGS. 10 and 11 can be obtained in which the outlines of the recognition marks are clear and from which an amount of misalignment can be detected.

Further, the inspector 105 according to the present embodiment adjusts the focus to the panel recognition mark, and then shifts the focus to capture the image of the component recognition mark. When the focus is adjusted to the panel recognition mark, the outer area of the component recognition mark is close to the inner area of the panel recognition mark, thereby making it difficult for the light to enter the area surrounding the component recognition mark.

Figure 10:
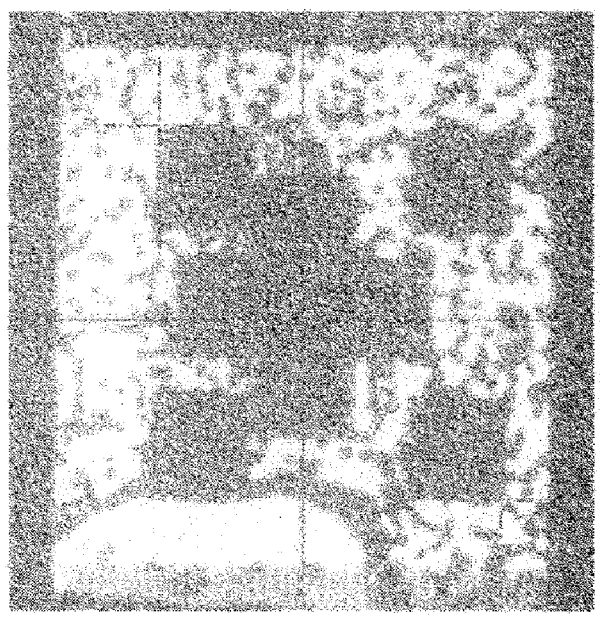
FIG. 10 shows an example of an image captured by an IR camera.
Figure 11:
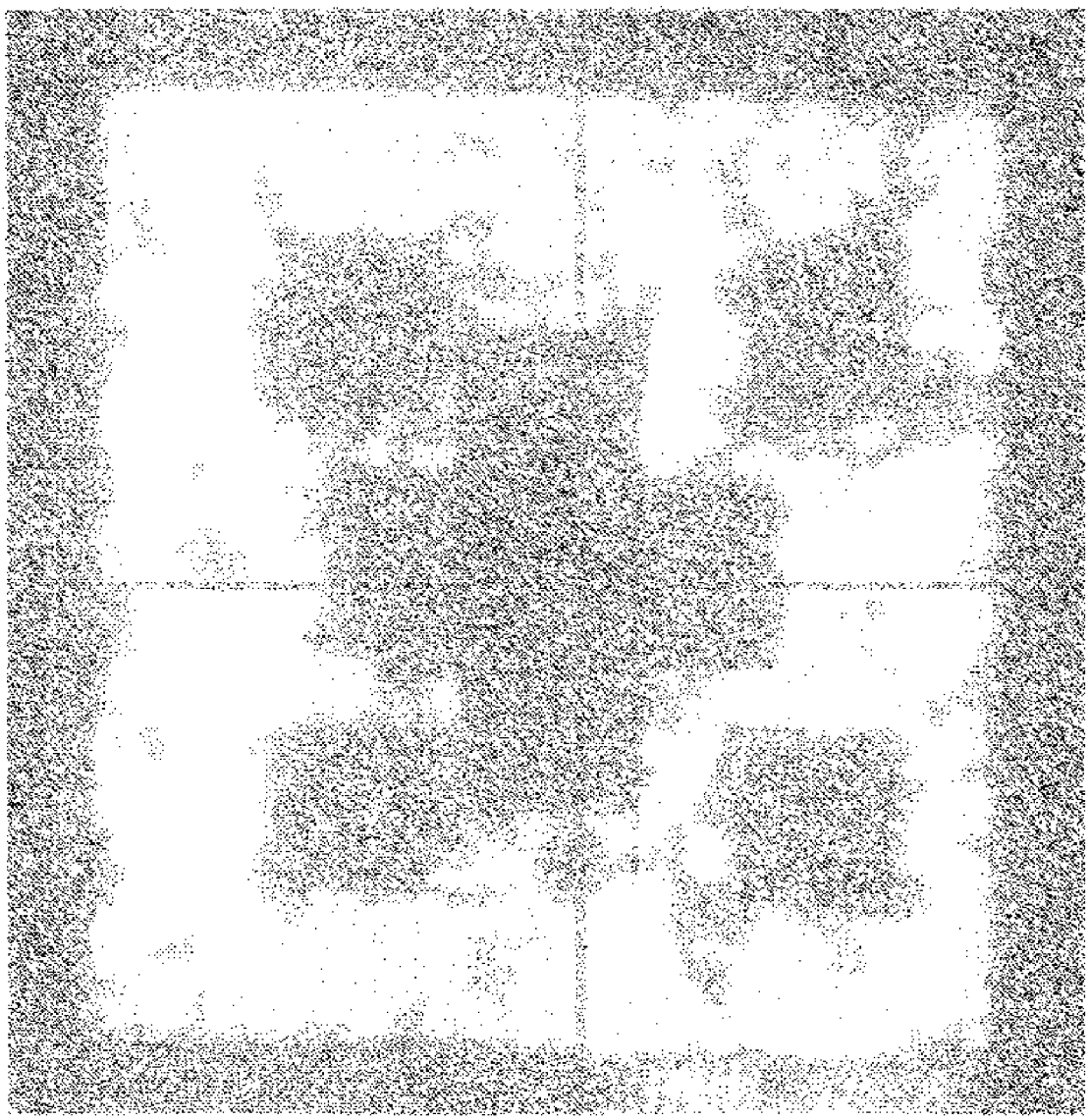
FIG. 11 shows an example of an image captured by an IR camera.

As a result, it is likely to obtain such images as shown in FIG. 10 in which the outlines of the recognition marks are unclear. However, shifting the focus allows the outline of the component recognition mark to appear clearly, making it possible to obtain such images as shown in FIG. 11 in which the outlines of the recognition marks are clear.

Furthermore, the inspector 105 according to the present embodiment performs the binarization after the interpolation on the captured image. Thus, the positions of the feature points can be more accurately obtained, and therefore it is possible to more precisely detect the amount of misalignment of the component mounted on the panel through the ACF.

Thus far, the inspection apparatus and the inspection method according to the present invention have been described above based on an embodiment, but the present invention is not limited to this embodiment. The present invention includes various modifications obvious to a person skilled in the art without departing from the scope of the present invention.

For example, the above embodiment has illustrated that the inspector is provided in the line. However, the panel mounter may have the function of inspecting the mounting-completed panel. In this case, the panel mounter has an infrared light illuminator and an IR camera arranged in the same positional relationship as in the inspector of the above embodiment.

Further, the above embodiment has illustrated that the captured image is interpolated and then binarized. The correction through the binarization, however, does not have to be performed, or may be replaced with correction using pattern matching. In the case of performing the pattern matching, an image of the component recognition mark and an image of a substrate recognition mark which are to be used as matching references are stored in the storage unit 441 of the inspector 105, and matching is performed between: the interpolated images of the component recognition mark and the substrate recognition mark; and the images of the component recognition mark and the substrate recognition mark stored in the storage unit 441.

Moreover, the above embodiment has illustrated that the inspector is provided with the infrared light illuminator and the IR camera to capture the image of the panel recognition mark and the image of the component recognition mark. However, the present invention is not limited by the above infrared light illuminator and IR camera as long as: the illuminator emits light which allows capturing of the image of the panel recognition mark and the image of the component recognition mark, that is, light having a wavelength which allows the light to pass through the panel and the component but does not allow or does not easily allow the light to pass through the conductive particles; and the camera can receive such light.

In addition, the above embodiment has illustrated that the obtaining unit obtains the position of one feature point from each of the panel recognition mark and the component recognition mark. However, the obtaining unit may obtain the positions of two feature points. This makes it possible also to calculate, as the amount of component misalignment, an amount of shift in the slope of a straight line connecting the two feature points and an amount of misalignment of the respective centers of the two feature points, thereby allowing more precise detection of the amount of misalignment of the component mounted on a flat panel through the ACF.

Further, the above embodiment has illustrated that the inspector calculates, using the panel recognition mark as a reference, the amount of misalignment of the component recognition mark as the amount of component misalignment. However, an amount of misalignment in a wiring pattern or a circuit pattern of the component may be calculated as the amount of component misalignment, using a wiring pattern of the panel as a reference.

Furthermore, the above embodiment has illustrated that the inspector corrects the image from which the conductive particles have been deleted. However, the conductive particles do not have to be deleted, and the inspector may correct an image containing the conductive particles. In this case, extracted from the captured image are: divided straight lines in the case where a combination of straight lines constitutes the shape of the recognition mark; and curves having a predetermined radius in the case where the recognition mark has a circular shape. Then, the interpolation is performed to connect the straight lines or to connect the curves.

Further, the present embodiment has illustrated that the focus is adjusted to the panel recognition mark to capture the image of the panel recognition mark, and then the focus is shifted to capture the image of the component recognition mark. However, the image of the component recognition mark may be captured without shifting the focus if the feature point of the component recognition mark is recognizable with the focus kept adjusted to the panel recognition mark. Further, the images of both the panel recognition mark and the component recognition mark may be captured after shifting the focus, without adjusting the focus to the panel recognition mark for the image capturing. In this case, images of the two recognition marks in which the feature points are recognizable can be simultaneously obtained, thereby reducing the time required for calculating the amount of misalignment.

Furthermore, the present embodiment has illustrated that the focus of the IR camera is shifted by a predetermined amount when it is determined that the feature point of the component recognition mark is not recognizable. However, the focus of the IR camera may be always shifted by a predetermined amount prior to capturing the image of the component recognition mark, without determining whether or not the feature point of the component recognition mark is recognizable. In this case, the storage unit 441 of the inspector holds, for example, a table associating the types of substrates and components (e.g. thickness of substrates and components) with amount of shift in the focus, and the inspector includes: an amount-of-shift determination unit which determines an amount of shift in the focus based on the table and the types of the substrate and the components constituting the mounting-completed panel to be inspected; and a recognition unit which recognizes the types of the substrate and components.

Moreover, the present embodiment has illustrated that the light in an amount which causes the average particle diameter of the conductive particles in the images captured by the IR camera 307 to be 80% or below of the actual average particle diameter is light intense enough to cause halation. However, it is possible to use, as the light intense enough to cause halation, light in an amount which causes the minimum luminance value to be higher than 15% of the maximum luminance value in a portion of the images captured by the IR camera 307 other than the portions of the panel recognition mark and the component recognition mark. This is based on measurement of luminance values (the average luminance value, the maximum luminance value, and the minimum luminance value of the portion of the images other than the portions of the panel recognition mark and the component recognition mark) of the images captured by the IR camera 307 shown in Table 1. That is to say, it is based on the result that the feature points are not recognizable when the images of the recognition marks are captured using light in an amount which causes the minimum luminance value to be 15% or below of the maximum luminance value.

TABLE 1

| Feature Point Regnition | Not possible | Not possible | Possible | Possible | Possible | Possible |
|---|---|---|---|---|---|---|
| Maximum Luminance Value | 255 | 255 | 255 | 255 | 255 | 255 |
| Minimum Luminance Value | 33 | 37 | 45 | 52 | 64 | 69 |
| Average Luminance Value | 166.3 | 183.3 | 201.3 | 213.3 | 221.6 | 230.3 |
| Relative Luminance Value Minimum Luminance Value/ Maximum Luminance Value | 13% | 15% | 18% | 20% | 25% | 27% |

Industrial Applicability

The present invention can be applied to inspection apparatuses and inspection methods, and particularly to component mounting systems and the like which mount components on panels.

The invention claimed is:

1. An inspection apparatus which detects an amount of misalignment, from a predetermined mounting position, of a component mounted on a surface of a panel through an adhesive which contains conductive particles, said inspection apparatus comprising:
   an illuminator which is provided on a bottom surface side of the panel which is opposite to a side of the panel on which the component is mounted, and illuminates with light a panel recognition mark formed on the panel and a component recognition mark formed on the component;
   a camera which is provided on a side of the panel opposite to said illuminator and captures an image of the panel recognition mark and an image of the component recognition mark which are illuminated with the light; and
   a calculation unit configured to calculate, using the images captured by said camera, an amount of misalignment in a positional relationship between the panel recognition mark and the component recognition mark from a predetermined positional relationship,
   wherein said illuminator emits light in an amount which causes halation in the images, the light having a wavelength that allows the light to pass through the panel and the component but does not allow or does not easily allow the light to pass through the conductive particles.

2. The inspection apparatus according to claim 1,
   wherein said illuminator emits light in an amount which causes an average particle diameter of the conductive particles in the images to be 80% or below of an actual average particle diameter.

3. The inspection apparatus according to claim 1,
   wherein said illuminator emits light in an amount which causes a minimum luminance value to be higher than 15% of a maximum luminance value in a portion of the images other than portions of the panel recognition mark and the component recognition mark.

4. The inspection apparatus according to claim 1, further comprising
   a focus adjustment unit configured to adjust a focus of said camera to one of the panel recognition mark and the component recognition mark and then to shift the focus of said camera by a predetermined amount.

5. The inspection apparatus according to claim 4, further comprising
   a determination unit configured to determine whether or not a feature point of the panel recognition mark and a feature point of the component recognition mark are recognizable in the images,
   wherein said focus adjustment unit is configured to shift the focus of said camera when said determination unit determines that the feature points are not recognizable.

6. The inspection apparatus according to claim 5, further comprising
   an obtaining unit configured to obtain a position of the feature point of the panel recognition mark and a position of the feature point of the component recognition mark in the images,
   wherein said calculation unit is configured to calculate an amount of misalignment of the feature point of one of the panel recognition mark and the component recognition mark from a predetermined position that is determined using the position of the feature point of the other one of the recognition marks as a reference.

7. An inspection method for detecting an amount of misalignment, from a predetermined mounting position, of a component mounted on a surface of a panel through an adhesive which contains conductive particles, said inspection method comprising:
   illuminating with light a panel recognition mark formed on the panel and a component recognition mark formed on the component, using an illuminator provided on a bottom surface side of the panel which is opposite to a side of the panel on which the component is mounted;
   capturing an image of the panel recognition mark and an image of the component recognition mark which are illuminated with the light, using a camera provided on a side of the panel opposite to the illuminator; and
   calculating, using the images captured by the camera in said capturing, an amount of misalignment in a positional relationship between the panel recognition mark and the component recognition mark from a predetermined positional relationship,
   wherein in said illuminating, light is emitted in an amount which causes halation in the images, the light having a wavelength that allows the light to pass through the panel and the component but does not allow or does not easily allow the light to pass through the conductive particles.

8. The inspection method according to claim 7,
   wherein in said illuminating, light is emitted in an amount which causes an average particle diameter of the conductive particles in the images to be 80% or below of an actual average particle diameter.

9. The inspection method according to claim 7,
   wherein in said illuminating, light is emitted in an amount which causes a minimum luminance value to be higher than 15% of a maximum luminance value in a portion of the images other than portions of the panel recognition mark and the component recognition mark.

10. The inspection method according to claim 7, further comprising:

adjusting a focus of the camera to one of the panel recognition mark and the component recognition mark; and shifting, by a predetermined amount, the focus adjusted to the one of the recognition marks, wherein said capturing includes: capturing an image of the one of the recognition marks to which the focus has been adjusted in said adjusting; and capturing an image of the other one of the recognition marks with the focus shifted in said shifting.

11. The inspection method according to claim 8, further comprising:

adjusting a focus of the camera to one of the panel recognition mark and the component recognition mark; and shifting, by a predetermined amount, the focus adjusted to the one of the recognition marks, wherein said capturing includes: capturing an image of the one of the recognition marks to which the focus has been adjusted in said adjusting; and capturing an image of the other one of the recognition marks with the focus shifted in said shifting.

12. The inspection method according to claim 9, further comprising:

adjusting a focus of the camera to one of the panel recognition mark and the component recognition mark; and shifting, by a predetermined amount, the focus adjusted to the one of the recognition marks, wherein said capturing includes: capturing an image of the one of the recognition marks to which the focus has been adjusted in said adjusting; and capturing an image of the other one of the recognition marks with the focus shifted in said shifting.

13. The inspection apparatus according to claim 2, further comprising a focus adjustment unit configured to adjust a focus of said camera to one of the panel recognition mark and the component recognition mark and then to shift the focus of said camera by a predetermined amount.

14. The inspection apparatus according to claim 3, further comprising a focus adjustment unit configured to adjust a focus of said camera to one of the panel recognition mark and the component recognition mark and then to shift the focus of said camera by a predetermined amount.

* * * * *